(12) United States Patent
Draper et al.

(10) Patent No.: US 10,064,996 B2
(45) Date of Patent: Sep. 4, 2018

(54) DRUG DELIVERY DEVICE

(71) Applicant: SANOFI-AVENTIS DEUTSCHLAND GMBH, Frankfurt am Main (DE)

(72) Inventors: Paul Richard Draper, Worcestershire (GB); George Cave, Warwickshire (GB); Joseph Butler, Warwickshire (GB); Samuel Steel, Warwickshire (GB); David Richard Mercer, Dorset (GB); Simon Bilton Lewis, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 423 days.

(21) Appl. No.: 14/763,863

(22) PCT Filed: Jan. 27, 2014

(86) PCT No.: PCT/EP2014/051468
§ 371 (c)(1),
(2) Date: Jul. 28, 2015

(87) PCT Pub. No.: WO2014/118105
PCT Pub. Date: Aug. 7, 2014

(65) Prior Publication Data
US 2015/0367074 A1    Dec. 24, 2015

(30) Foreign Application Priority Data
Jan. 29, 2013   (EP) ..................................... 13153132

(51) Int. Cl.
*A61M 5/31*    (2006.01)
*A61M 5/32*    (2006.01)
(Continued)

(52) U.S. Cl.
CPC ................ *A61M 5/31* (2013.01); *A61M 5/20* (2013.01); *A61M 5/3202* (2013.01);
(Continued)

(58) Field of Classification Search
CPC .... A61M 5/31; A61M 5/3202; A61M 5/3204; A61M 5/31565; A61M 5/31566;
(Continued)

(56) References Cited

U.S. PATENT DOCUMENTS 5,401,251 A * 3/1995 Hui ..................... A61M 5/3216
 604/192
8,361,026 B2 * 1/2013 Edwards ............... A61M 5/002
 206/363

(Continued)

FOREIGN PATENT DOCUMENTS

WO  2008/045203  4/2008
WO  2009/113060  9/2009
(Continued)

OTHER PUBLICATIONS

European Search Report for EP App. No. 13153132.9, dated Jun. 28, 2013.
(Continued)

*Primary Examiner* — Andrew Gilbert
(74) *Attorney, Agent, or Firm* — Fish & Richardson P.C.

(57) ABSTRACT

A drug delivery device for administering a drug is presented having a body, at least one electrical unit and a port for electrically contacting the electrical unit, an adapter for attaching an injection needle to the drug delivery device, a safety mechanism arranged to prevent contacting the electrical unit whilst an injection needle is in fluid communication with the drug delivery device and arranged to prevent establishing a fluid communication while the electrical unit is contactable.

9 Claims, 15 Drawing Sheets

(51) Int. Cl.
*A61M 5/20* (2006.01)
*A61M 5/24* (2006.01)
*A61M 5/34* (2006.01)

(52) U.S. Cl.
CPC ............. *A61M 5/3204* (2013.01); *A61M 5/24* (2013.01); *A61M 5/345* (2013.01); *A61M 2005/206* (2013.01); *A61M 2205/14* (2013.01); *A61M 2205/50* (2013.01); *A61M 2205/502* (2013.01); *A61M 2205/8237* (2013.01); *A61M 2205/8262* (2013.01)

(58) Field of Classification Search
CPC ............ A61M 5/3157; A61M 5/31571; A61M 5/31573; A61M 2205/14
See application file for complete search history.

(56) References Cited

U.S. PATENT DOCUMENTS

| | | | | |
|---|---|---|---|---|
| 8,657,787 | B2* | 2/2014 | Neer | A61M 5/14546 604/156 |
| 8,817,258 | B2* | 8/2014 | Whalley | A61M 5/31 356/432 |
| 9,339,605 | B2* | 5/2016 | Wimpenny | A61M 5/002 |
| 2002/0193679 | A1* | 12/2002 | Malave | A61B 5/0095 600/407 |
| 2004/0069798 | A1* | 4/2004 | Grey | A61J 7/0481 222/52 |
| 2011/0009824 | A1* | 1/2011 | Yodfat | A61M 5/14248 604/151 |
| 2012/0289858 | A1* | 11/2012 | Ouyang | A61B 10/0275 600/562 |
| 2013/0079708 | A1* | 3/2013 | Wimpenny | A61M 5/002 604/65 |
| 2013/0310756 | A1* | 11/2013 | Whalley | A61M 5/31 604/189 |
| 2014/0142507 | A1* | 5/2014 | Armes | A61M 5/422 604/112 |
| 2014/0243749 | A1* | 8/2014 | Edwards | A61M 5/31 604/187 |
| 2014/0296824 | A1* | 10/2014 | Edwards | A61M 5/002 604/506 |
| 2014/0311227 | A1* | 10/2014 | Koski | G01N 27/3273 73/61.41 |
| 2015/0021243 | A1* | 1/2015 | Herrington | C02F 1/002 210/85 |
| 2015/0294551 | A1* | 10/2015 | Edwards | A61M 5/31 340/635 |
| 2015/0320932 | A1* | 11/2015 | Draper | A61M 5/20 604/131 |
| 2015/0359967 | A1* | 12/2015 | Steel | A61M 5/345 604/192 |
| 2015/0359968 | A1* | 12/2015 | Steel | A61M 5/20 604/189 |
| 2015/0367075 | A1* | 12/2015 | Cave | A61M 5/20 604/241 |
| 2016/0263324 | A1* | 9/2016 | Shaanan | A61M 5/14566 |
| 2016/0296700 | A1* | 10/2016 | Kikuchi | A61M 5/36 |
| 2017/0106145 | A1* | 4/2017 | Draper | A61M 5/20 |

FOREIGN PATENT DOCUMENTS

WO 2011/117404 9/2011
WO WO2011117404 A1 * 9/2011

OTHER PUBLICATIONS

International Search Report and Written Opinion for Int. App. No. PCT/EP2014/051468, dated Apr. 7, 2014.

* cited by examiner

DRUG DELIVERY DEVICE

CROSS REFERENCE TO RELATED APPLICATIONS

The present application is a U.S. National Phase Application pursuant to 35 U.S.C. § 371 of International Application No. PCT/EP2014/051468 filed Jan. 27, 2014 which claims priority to European Patent Application No. 13153132.9 filed Jan. 29, 2013. The entire disclosure contents of these applications are herewith incorporated by reference into the present application.

TECHNICAL FIELD

The invention relates to a drug delivery device.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring. In other devices this is achieved by an electromechanical drive. Devices with electromechanical and/or electronic components may comprise a port which may serve for wired communication with another device for data transfer or for charging.

WO 2011/117404 A2 discloses an electro-mechanical drug delivery device comprising a main body having a distal end and a proximal end. The distal end is configured to attach to a dispense interface. A separable housing that can prevent an administration of a drug by the drug delivery device, the housing configured to cover at least a portion of the distal end of the main body when the separable housing is coupled to the main body of the drug delivery device. A conduction element is provided by the main body and configured for establishing an electrical connection with an electrical connector. Establishment of the electrical connection is prevented when the housing does not cover at least a portion of the distal end of the main body. The electrical connection may be established when the housing covers at least a portion of the distal end of the main body of the drug delivery device.

SUMMARY

It is an object of the present invention to provide an improved drug delivery device.

The object is achieved by a drug delivery device according to claim 1.

Preferred embodiments of the invention are given in the dependent claims.

According to the invention a drug delivery device for administering a drug comprises:
- a body,
- at least one electrical unit and a port for electrically contacting the electrical unit,
- an adapter for attaching an injection needle to the drug delivery device,
- a safety mechanism arranged to prevent contacting the electrical unit whilst an injection needle is in fluid communication with the drug delivery device and arranged to prevent establishing a fluid communication whilst the electrical unit is contactable.

The body may house a syringe or cartridge.

The port, e.g. a USB port, may serve for wired communication with another device for data transfer or charging. The safety mechanism avoids the risk that the user may inadvertently leave the drug delivery device connected via a cable whilst attempting to inject. In this case there may exist a potential conductive path from the externally connected device, through the cable, the port and the electronics of the drug delivery device to the patient via the conductive metal injection needle. In case of a current overload on the port or a leaking cartridge which creates a short-circuit within the drug delivery device, the patient would be subjected to an electric shock. An electric shock may occur either if both the patient and the external device connected to the port are grounded or if the patient touches the port whilst they were injecting regardless of whether a cable is connected to the port or not. Similarly, the port may be adapted to interface with a blood glucose strip for measuring a user's blood glucose value. The port will thus also feature electronic contacts. Consequently there is a similar associated risk.

The above risk is addressed by providing a safety mechanism arranged to prevent access to the port whilst an injection needle is in fluid communication with the cartridge and arranged to prevent establishing a fluid communication between an injection needle and the cartridge whilst the port is accessible.

Other options would be to have the safety mechanism disable the dosing operation of the drug delivery device when the user can access the port. This may be achieved by performing an operation which disables a delivery mechanism of the drug delivery device or by preventing the user from accessing a button or soft button on a human-machine interface for operating the drug delivery device.

In an exemplary embodiment the safety mechanism comprises a docking station comprising a universal connector and a customized connector to attach to the port of the drug delivery device, wherein the docking station furthermore comprises a portion arranged such that the drug delivery device can only be inserted into the docking station without a needle or needle arrangement attached.

In an exemplary embodiment the port is arranged within a recess in the body, wherein the safety mechanism comprises a cover arranged to hide the recess when in a closed position or expose the recess when in an open position relative to the body, wherein a cap is arranged to be assembled over the needle and over part of the body such that the needle is inaccessible when the cap is attached to the body, whereas the recess with the port remains uncovered, wherein the cap, when mounted to the body, is arranged to cause movement of the cover into the open position and/or unlock the cover for allowing its movement into the open position.

In an exemplary embodiment a first spring is arranged to bias the cover towards the closed position thus ensuring that the port is automatically rendered inaccessible on removal of the cap.

In an exemplary embodiment of the cover is arranged to pivot or slide between the closed position and the open position.

In an exemplary embodiment the cover is arranged to be locked in the closed position thus preventing the user from exposing the port.

In an exemplary embodiment a blocking component is slidably arranged in the body and biased towards a blocking position for preventing the cover to be moved out of the closed position, wherein the cap, when attached to the body, is arranged to move the blocking component out of the blocking position thus allowing movement of the cover towards the open position.

In an exemplary embodiment the blocking component is shaped as a third spring, wherein the cover is shaped substantially cylindrical, rotatably fitted to the body and comprises an opening for accessing the port, wherein when the cap is not fitted to the body, a retaining tongue on the third spring engages with a retaining feature on the cover to prevent it from rotating out of the closed position, wherein a beam on the cap is arranged to push the third spring out of engagement with the retaining feature when the cap is mounted to the body.

In an exemplary embodiment a handle on the cover is arranged to interact with an opening in the cap such that the cap prevents rotation of the cover unless it is assembled to the body.

In an exemplary embodiment the cap is arranged to be mounted to the body by an axial translation and/or a rotation.

In an exemplary embodiment the port is arranged within a recess in the body, wherein the safety mechanism comprises the port being movable relative to the body, wherein a cap is arranged to be assembled over the needle and over part of the body such that the needle is inaccessible when the cap is attached to the body, whereas the recess with the port remains uncovered, wherein the cap, when mounted to the body, is arranged to cause movement of the port into alignment with the recess in an open position and wherein the port moves into misalignment with the recess when the cap is removed from the body.

In an exemplary embodiment a switch is arranged in the body for detecting the cap such that assembling the cap to the body triggers the switch which causes release of a retaining mechanism for moving or allowing movement of the cover and/or the port into the open position for rendering the port accessible and that removal of the cap triggers the switch which causes the retaining mechanism to move the cover and/or the port (5) into the closed position.

In an exemplary embodiment removal of the cap is prevented while a connector is connected to the port.

In an exemplary embodiment the port is arranged within a recess in the body, wherein the safety mechanism comprises a blocking component biased to protrude into the recess to prevent a connector from connecting to the port, wherein a cap is arranged to be assembled over the needle and over part of the body such that the needle is inaccessible when the cap is attached to the body, whereas the recess with the port remains uncovered, wherein the cap, when attached, is arranged to move the blocking component away from the port thus allowing a connector to be fitted to the port.

In an exemplary embodiment the safety mechanism comprises the port being arranged within a cap arranged to be assembled over the needle and over part of the body such that the needle is inaccessible when the cap is attached to the body, wherein an interface between the body and the cap comprises a connector and a second port is arranged to connect the port to the body when the cap is attached to the body.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
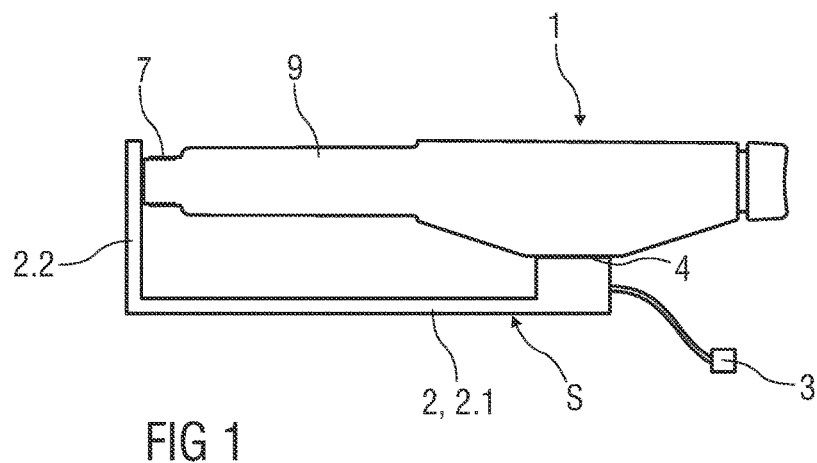
FIG. 1 is a schematic view of a first exemplary embodiment of an electromechanical drug delivery device arranged within a docking station.

FIG. 1 is a schematic view of a first exemplary embodiment of an electromechanical drug delivery device 1 for administering a drug. The drug delivery device 1 comprises a body 9 adapted to receive a drug cartridge or syringe (not illustrated). A hypodermic needle (not illustrated) may be attached to the cartridge. The drug delivery device 1 may comprise at least one electrical unit EU such as a human-machine-interface for communicating information to a user and for allowing the user to operate the drug delivery device 1. Furthermore, the electrical unit EU may be an electromechanical drive (not illustrated) for inserting the needle into an injection site, e.g. a patient's skin and/or dispensing drug from the cartridge through the needle and/or retracting the needle post-injection.

The needle may be attached and removed by the user thus allowing it to be used for a single delivery of the drug. After delivery the needle is removed, discarded and replaced by a new one, if applicable.

The drug delivery device 1 comprises a port 5 (cf. FIG. 2) which may serve for wired communication with another device for data transfer or charging. There is an associated risk with this feature that the user may inadvertently leave the drug delivery device 1 connected via a cable whilst attempting to inject. Whilst a control unit of the drug delivery device 1 may run software including checks to prevent the delivery of the drug in this situation, there will still exist a potential conductive path from the externally connected device, through the cable, the port 5 and the electronics of the drug delivery device 1 to the patient via the conductive metal injection needle. It is thus possible that, for instance, a current overload on the port 5 or a leaking cartridge which creates a short-circuit within the drug delivery device 1, could deliver an electric shock to the patient. This may occur either if both the patient and the external device connected to the port 5 are grounded or if the patient touches the port 5 whilst they were injecting regardless of whether a cable is connected to the port 5 or not.

Similarly, the port 5 may be adapted to interface with a blood glucose strip for measuring a user's blood glucose value. The port 5 will thus also feature electronic contacts. Consequently there is a similar associated risk.

The above risk is addressed by providing a safety mechanism S to disable the dosing operation of the drug delivery device 1 when the user can access the port 5. This is achieved by performing an operation which disables a delivery mechanism of the drug delivery device 1 or by preventing the user from accessing an adapter 7 such as a threaded area 7 of the drug delivery device 1 adapted to connect to the needle or from accessing a button or soft button on the human-machine interface.

FIG. 1 is a schematic side view of a drug delivery device 1 arranged within a docking station 2. The docking station 2 as part of the safety mechanism S comprises a universal connector 3 to attach to a computational device such as a computer, e.g. a personal computer or a laptop, and a bespoke or customized connector 4 to attach to the drug delivery device 1. The bespoke connector 4 ensures the docking station 2 is used for connecting the drug delivery device 1 instead of a readily available standard lead.

The docking station 2 comprises a longitudinal portion 2.1 which the bespoke connector 4 is transversally arranged on for connecting to the port 5 (cf. FIG. 2) laterally arranged in the drug delivery device 1. A transversal portion 2.2 is arranged on the longitudinal portion 2.1 of the docking station 2 such that the drug delivery device 1 can only be inserted into the docking station 2 without a needle or needle arrangement attached. Otherwise the needle or needle arrangement would collide with the transversal portion 2.2 thus preventing insertion into the docking station 2. Thus the drug delivery device 1 can either have a needle attached while access to its port 5 is being prevented or have its port 5 connected to the connector 4 while being prevented from attaching a needle thus mitigating the above described risk.

Figure 2:
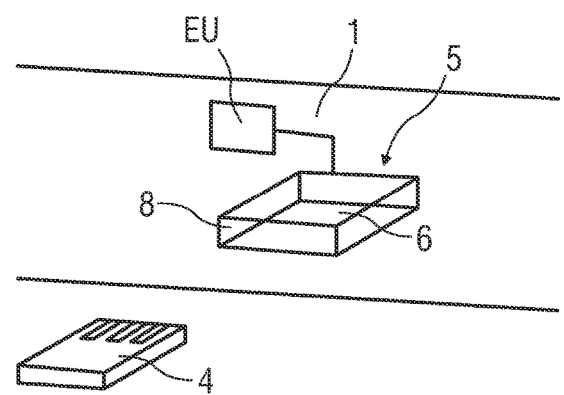
FIG. 2 is a schematic perspective detail view of the drug delivery device with the docking station.

FIG. 2 is a schematic perspective detail view of the drug delivery device 1 with the docking station 2. The port 5 is arranged within a relatively deep recess 6 accessible through a relatively small aperture 8 in the body 9 of the drug delivery device 1. The bespoke connector 4 on the docking station 2 is accordingly long. The hardly accessible port 5 prevents a user from tampering with the drug delivery device 1 trying to connect a readily available standard lead.

Figure 3:
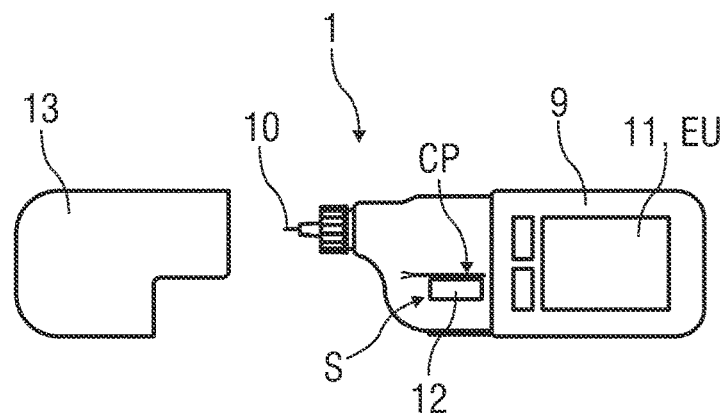
FIG. 3 is a schematic view of a second exemplary embodiment of a drug delivery device with a cap removed from a body.

FIG. 3 is a schematic view of a second exemplary embodiment of a drug delivery device 1. The drug delivery device 1 comprises a body 9 adapted to receive a drug cartridge or syringe (not illustrated). A hypodermic needle 10 may be attached to the cartridge. The drug delivery device 1 may comprise a human-machine-interface 11 for communicating information to a user and for allowing the user to operate the drug delivery device 1. Furthermore, the drug delivery device may comprise an electromechanical drive (not illustrated) for inserting the needle 10 into an injection site, e.g. a patient's skin and/or dispensing drug from the cartridge through the needle 10 and/or retracting the needle 10 post-injection.

The needle 10 may be attached and removed by the user thus allowing it to be used for a single delivery of the drug. After delivery the needle 10 is removed, discarded and replaced by a new one, if applicable.

The drug delivery device 1 comprises a port 5 (cf. FIG. 5) which may serve for wired communication with another device for data transfer or charging. The port 5 is arranged within a recess 6 in the body 9 of the drug delivery device 1. A sliding cover 12 is arranged to hide the recess 6 when in a closed position CP or expose the recess 6 when in an open position OP relative to the body 9.

A cap 13 is arranged to be assembled over the needle 10 and over part of the body 9 such that the needle 10 is inaccessible when the cap 13 is attached to the body 9, whereas the recess 6 with the port 5 remains uncovered. The sliding cover 12 is arranged to engage the cap 13 such that the sliding cover 12 is in the closed position CP when not engaged by the cap 13 and in the open position OP when the cap 13 is fully mounted to the body 9 of the drug delivery device 1.

FIG. 3 shows the drug delivery device 1 with the cap 13 removed from the body 9. The cover 12 is thus in the closed position CP such that the port 5 is inaccessible.

Figure 4:
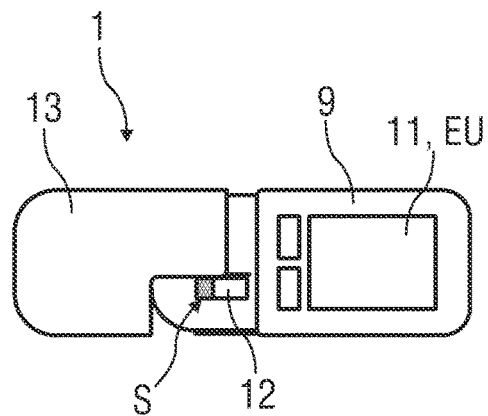
FIG. 4 is a schematic view of the second exemplary embodiment of the drug delivery device while the cap is being attached to the body.

FIG. 4 shows the drug delivery device 1 while the cap 13 is being attached to the body 9. The cover 12 is thus moved from the closed position CP towards the open position OP such that the port 5 is partially exposed but cannot yet be accessed.

Figure 5:
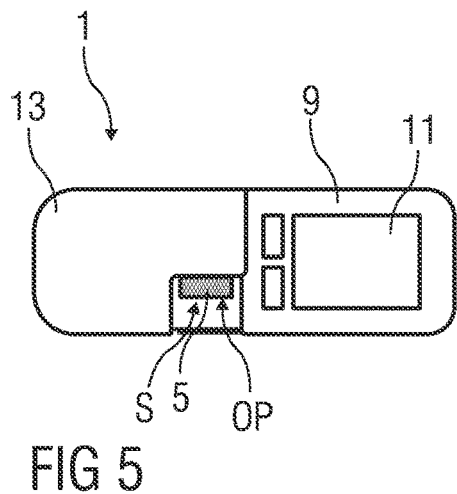
FIG. 5 is a schematic view of the second exemplary embodiment of the drug delivery device with the cap fully attached to the body.

FIG. 5 shows the drug delivery device 1 with the cap 13 fully attached to the body 9. The cover 12 is thus in the open position OP such that the port 5 is accessible.

Figure 6:
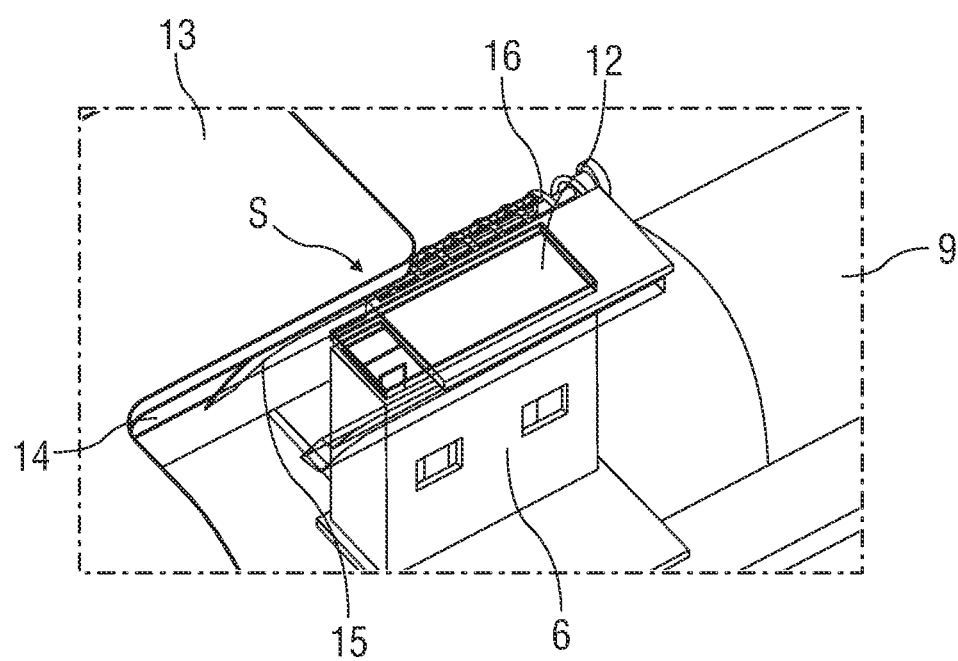
FIG. 6 is a schematic perspective view of a detail of the drug delivery device with a port and a sliding cover.

FIG. 6 is a schematic perspective view of a detail of the drug delivery device 1 with the port 5 and the sliding cover 12. A tab 14 on the cap 13 is adapted to interface with a slot 15 in the body 9, acting on the sliding cover 12 to move it axially internally within the body 9. This action also compresses a first spring 16 which is used to restore the sliding cover to the closed position CP once the cap 13 is removed.

In an alternative embodiment the cover 12 may be pivoted instead of slid such that it rotates about one of its edges or corners between the open position OP and the closed position CP.

Figure 7:
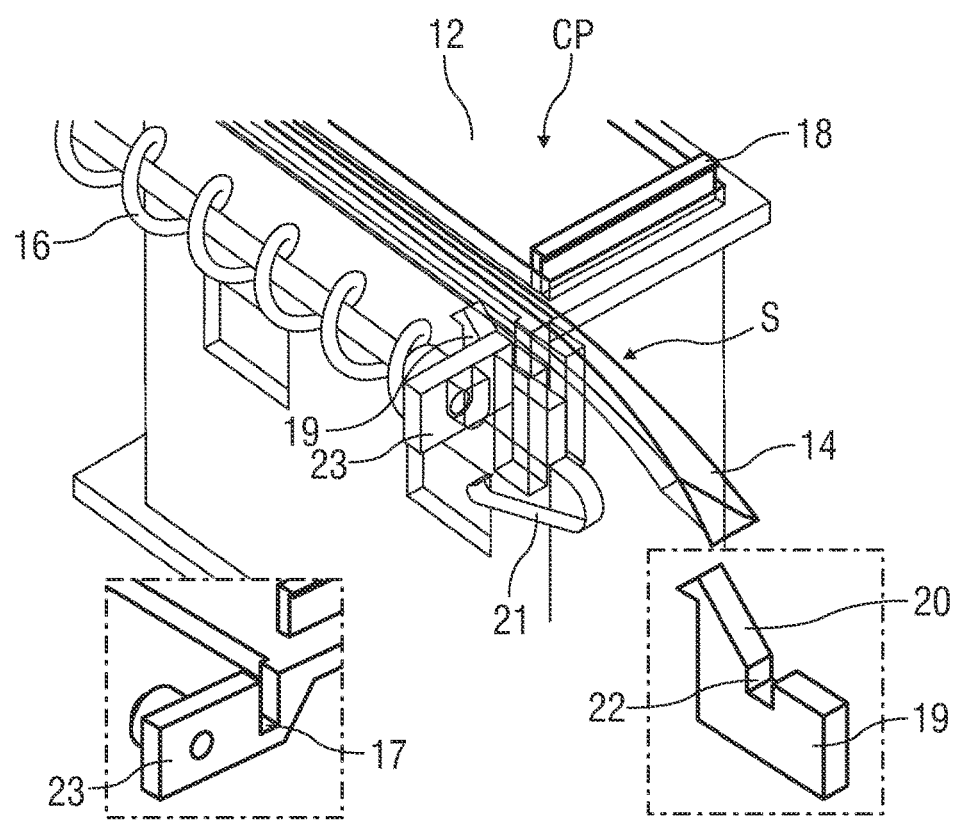
FIG. 7 is a schematic detail view of an exemplary embodiment of a safety mechanism.

FIG. 7 is a schematic detail view of an exemplary embodiment of the safety mechanism.

In this alternative embodiment the cover 12 may not be slid into the open position OP by the cap 13 but just unlocked such that a user may manually slide the cover 12 open, while the cover 12 remains locked without the cap 13 attached thus preventing the user from exposing the port 5. For this purpose the sliding cover 12 may be modified to incorporate a slot 17 to allow the tab 14 on the cap 13 to pass freely through it. A cover handle 18 may be arranged to allow the user to move the cover 12 into the open position OP. The first spring 16 remains to bias the sliding cover 12 towards the closed position CP.

A blocking component 19 with a chamfered section 20 is slidably arranged in the body 9 and outwardly biased towards a blocking position by a second spring 21. The blocking component 19 comprises a blocking recess 22 for engaging a blocking protrusion 23 on the cover 12 when the cover 12 is in the closed position CP and the blocking component 19 is in the blocking position.

As the cap 13 is fitted to the body 9 of the drug delivery device 1, the tab 14 on the cap 13 (cf. FIG. 6) is slid through the slot 17 and acts on the chamfered section 20 of the blocking component 19 to push it down, i.e. laterally into the body 9. Once the blocking component 19 has moved far enough inwards it releases the blocking protrusion 23 such that the user is able to operate the cover handle 18 to retract the sliding cover 12 into the open position OP against the force of the first spring 16. When the cap 13 is removed from the body 9, the procedure occurs in reverse, the first spring 16 moves the cover 12 towards the closed position CP and the second spring 21 moves the blocking component 19 towards the outward position such that the blocking component 19 re-engages the blocking protrusion 23 on the cover 12. The user is unable to open the sliding cover 12 without the cap 13 fitted as the blocking component 19 prevents the sliding cover 12 from moving.

The embodiment shown in FIG. 7 prevents the user from inadvertently, or deliberately, sliding back the cover 12 whilst the cap 13 is removed using either their finger or a small implement.

Figure 8:
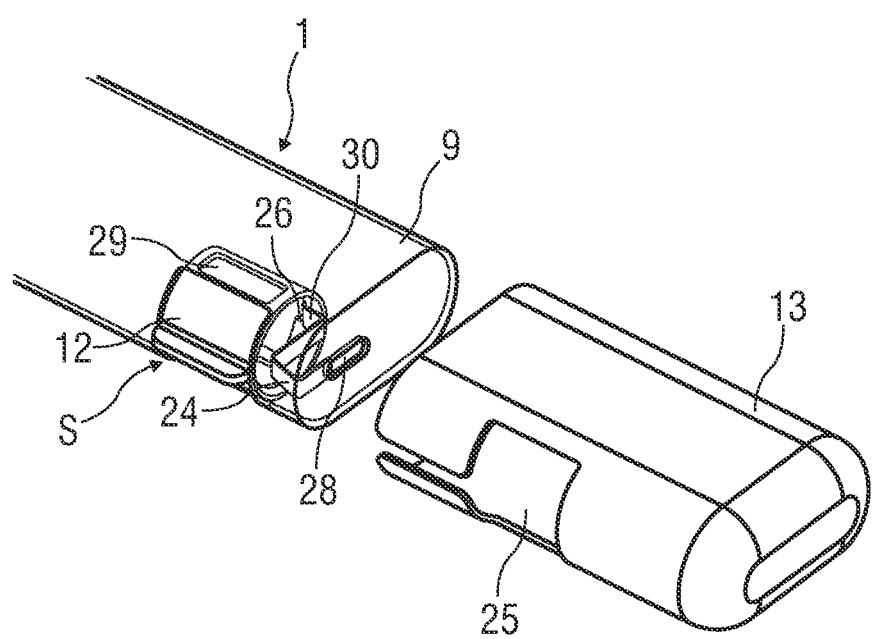
FIG. 8 is a schematic view of an alternative embodiment of the safety mechanism comprising a third spring and a substantially cylindrical cover rotatably fitted within the body.

An alternative embodiment, which also has the effect of restricting the motion of the cover 12 unless the cap 13 is fitted, is illustrated in FIG. 8. The embodiment comprises a blocking component shaped as a third spring 24 and a substantially cylindrical cover 12 rotatably fitted within the body 9. When the cap 13 is not fitted to the body 9, a retaining tongue 30 on the third spring 24 engages with a retaining feature 26 on the cover 12 to prevent it from rotating.

Figure 9:
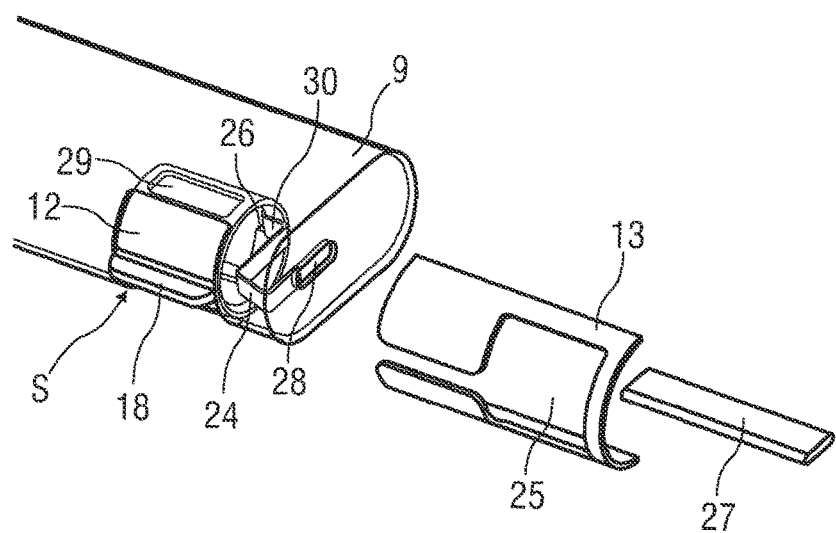
FIG. 9 is a schematic view of the embodiment of FIG. 8 in an initial state.
Figure 10:
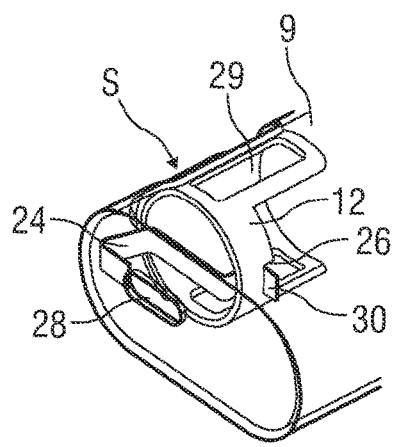
FIG. 10 is another schematic view of the embodiment of FIG. 8 in an initial state.
Figure 11:
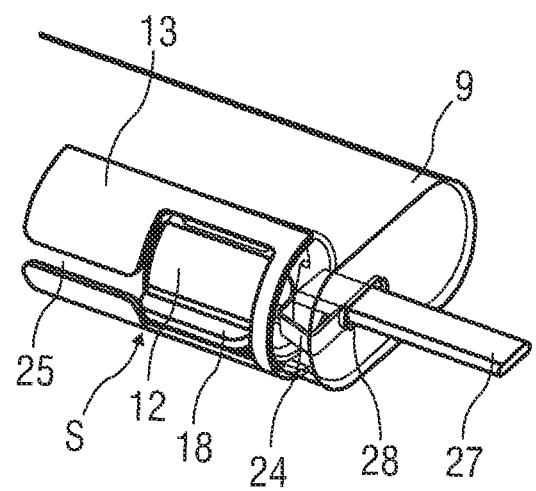
FIG. 11 is a schematic view of the embodiment of FIG. 8 with the cap fitted to the body.
Figure 12:
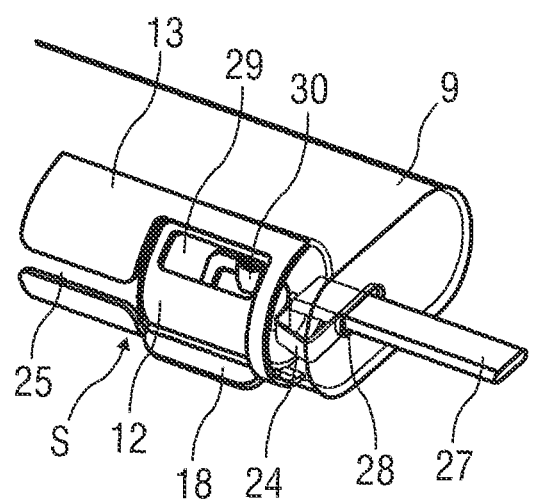
FIG. 12 is a schematic view of the embodiment of FIG. 8 with the cover rotated for accessing the port.

FIGS. 9 to 12 illustrate the operation of this embodiment. A portion of the cap 13 has been removed for clarity. In an initial state as illustrated in FIGS. 9 and 10, the retaining feature 26 on the cover 12 interfaces with the third spring 24 to prevent the user from operating and rotating the cover 12. When the cap 13 is fitted to the body 9, a beam 27 on the cap 13 pushes through an aperture 28 in the body 9 to move the third spring 24 away from the cover 12 and out of engagement with the retaining feature 26 (see FIG. 11). This allows the user to operate and rotate the cover 12 and gain access to the port 5 through an opening 29 in the cover 12 (see FIG. 12).

A handle 18 on the cover 12 may interact with an opening 25 in the cap 13 such that the cap 13 prevents rotation of the cover 12 unless it is fully assembled to the body 9.

Figure 13:
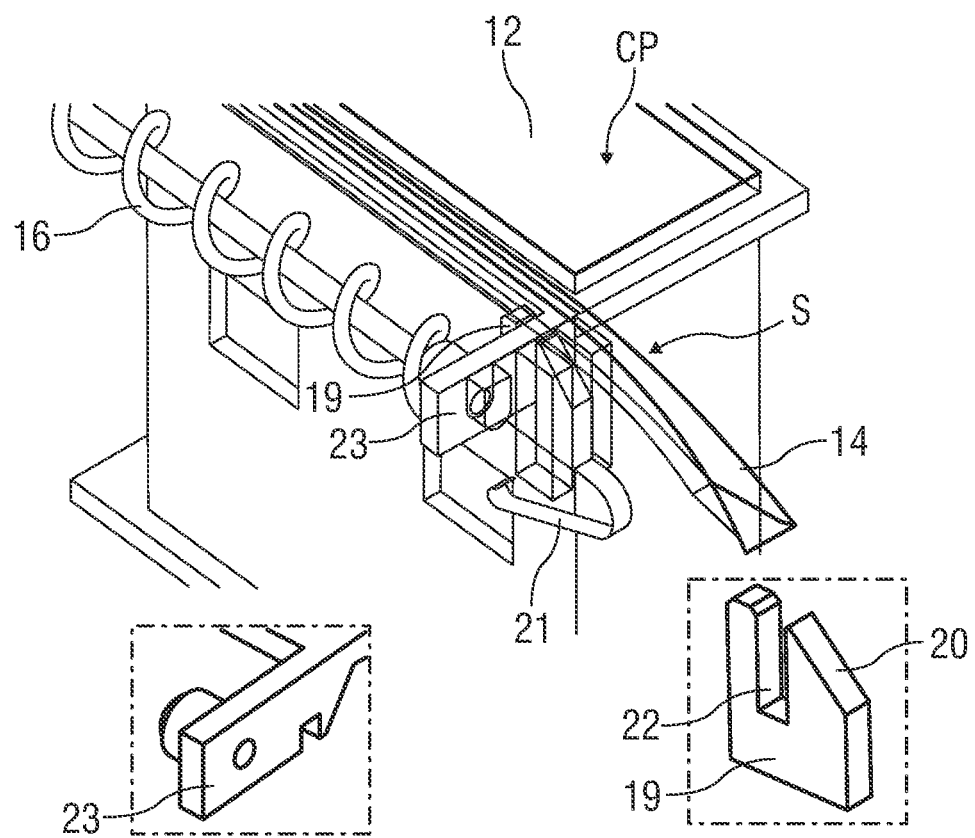
FIG. 13 is a perspective view of an alternative embodiment of the safety mechanism.

FIG. 13 is a perspective view of an alternative embodiment of the safety mechanism. In this embodiment the cap 13 is allowed to both actuate the blocking component 19 and retract the sliding cover 12 towards the open position OP. In FIG. 13 the embodiment of FIG. 7 is modified to make the tab 14 on the cap 13 actuate the sliding cover 12 in addition to moving the chamfered section 20 on the blocking component 19 sufficiently so that it is actuated before the tab 14 on the cap 13 contacts the sliding cover 12. This is achieved by arranging the chamfered section 20 and the blocking recess 22 on the blocking component 19 such that the tab 14 on the cap 13 engages the chamfered section 20 before reaching the blocking recess 22 when the cap 13 is being fitted to the body 9. As opposed to this in FIG. 7 the tab 14 reaches the blocking recess 22 before the chamfered section 20 when the cap 13 is being fitted to the body 9.

Figure 14:
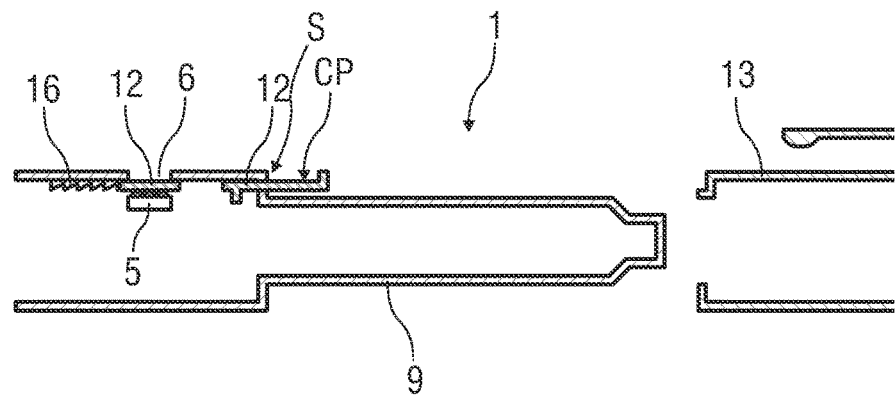
FIG. 14 is a schematic longitudinal section of an exemplary embodiment of the drug delivery device prior to assembly of the cap with the cover in a closed position.
Figure 15:
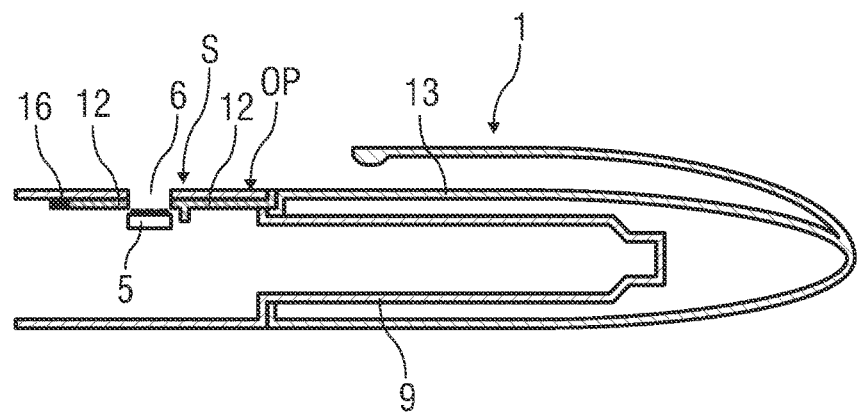
FIG. 15 is a schematic longitudinal section of the drug delivery device of FIG. 14 with the assembled cap and with the cover in an open position

FIGS. 14 and 15 illustrate an embodiment whose features may be combined with any of the embodiments described in this specification.

The drug delivery device 1 comprises a body 9 adapted to receive a drug cartridge or syringe (not illustrated). A hypodermic needle (not illustrated) may be attached to the cartridge. The drug delivery device 1 may comprise a human-machine-interface (not illustrated) for communicating information to a user and for allowing the user to operate the drug delivery device 1. Furthermore, the drug delivery device may comprise an electromechanical drive (not illustrated) for inserting the needle into an injection site, e.g. a patient's skin and/or dispensing drug from the cartridge through the needle and/or retracting the needle post-injection.

The needle may be attached and removed by the user thus allowing it to be used for a single delivery of the drug. After delivery the needle is removed, discarded and replaced by a new one, if applicable.

The drug delivery device 1 comprises a port 5 which may serve for wired communication with another device for data transfer or charging. The port 5 is arranged within a recess 6 in the body 9 of the drug delivery device 1. A sliding cover 12 is arranged to hide the recess 6 when in a closed position CP or expose the recess 6 when in an open position OP relative to the body 9.

A cap 13 is arranged to be assembled over the needle and over part of the body 9 such that the needle is inaccessible when the cap 13 is attached to the body 9, whereas the recess 6 with the port 5 remains uncovered. The sliding cover 12 is arranged to engage the cap 13 such that the sliding cover 12 is in the closed position CP when not engaged by the cap 13 and in the open position OP when the cap 13 is fully mounted to the body 9 of the drug delivery device 1.

As opposed to the aforementioned embodiments, where the sliding cover 12 is arranged within the body 9, in the embodiment of FIGS. 14 and 15 the sliding cover 12 is arranged partially or entirely outside of the body 9.

FIG. 14 is a schematic longitudinal section of the drug delivery device 1 prior to assembly of the cap 13 with the cover 12 in the closed position CP. The first spring 16 biases the sliding cover 12 towards the closed position CP such that the cover is closed 12 when the cap 13 is removed from the body 9. FIG. 15 is a schematic longitudinal section of the drug delivery device 1 with the assembled cap 13 and with the cover 12 in the open position OP.

The embodiments as outlined above make use of components actuated to operate in a linear fashion. An alternative embodiment would apply the same principles to a cap 13 fitted with a rotary motion as opposed to a linear motion. As the cap 13 is fitted to the body 9, the cover 12 rotates about a central axis of the body 9, to reveal the port 5.

The mechanism may be adapted to execute the motion in any of the following ways:

The cap 13 rotates onto the body 9, causing the cover 12 to rotate within the body 9.

The cap 13 attaches axially onto the body 9 and then rotates at the end of its travel, causing the cover 12 to rotate within the body 9.

The cap 13 attaches axially onto the body 9 with no rotation of the cap 13 taking place, but still causing the cover 12 to rotate within the body 9.

Figure 16:
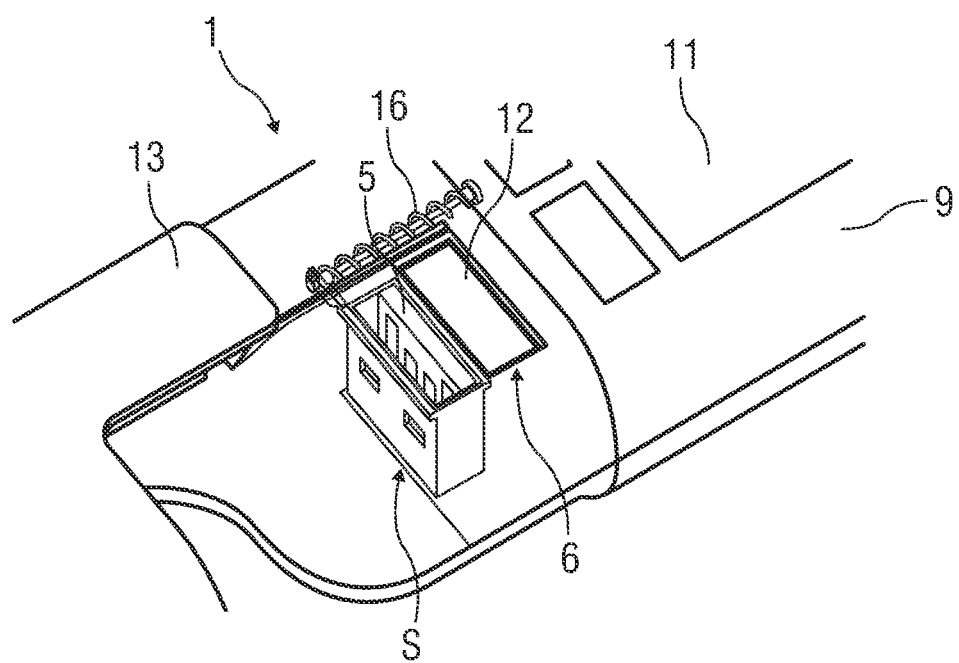
FIG. 16 is a schematic perspective view of another exemplary embodiment of a drug delivery device with the cap removed and the port is misaligned with a recess.

FIG. 16 is a schematic perspective view of another exemplary embodiment of a drug delivery device 1.

The drug delivery device 1 comprises a body 9 adapted to receive a drug cartridge or syringe (not illustrated). A hypodermic needle (not illustrated) may be attached to the cartridge. The drug delivery device 1 may comprise a human-machine-interface 11 for communicating information to a user and for allowing the user to operate the drug delivery device 1. Furthermore, the drug delivery device 1 may comprise an electromechanical drive (not illustrated) for inserting the needle into an injection site, e.g. a patient's skin and/or dispensing drug from the cartridge through the needle and/or retracting the needle post-injection.

The drug delivery device 1 comprises a port 5 which may serve for wired communication with another device for data transfer or charging. The port 5 is arranged in the body 9 of the drug delivery device 1. The port 5 is moveably arranged within the body 9 such that it may be aligned or misaligned with a recess 6 in the body 9 thus rendering the port 5 accessible or inaccessible.

A cap 13 is arranged to be assembled over the needle and over part of the body 9 such that the needle is inaccessible when the cap 13 is attached to the body 9.

Figure 17:
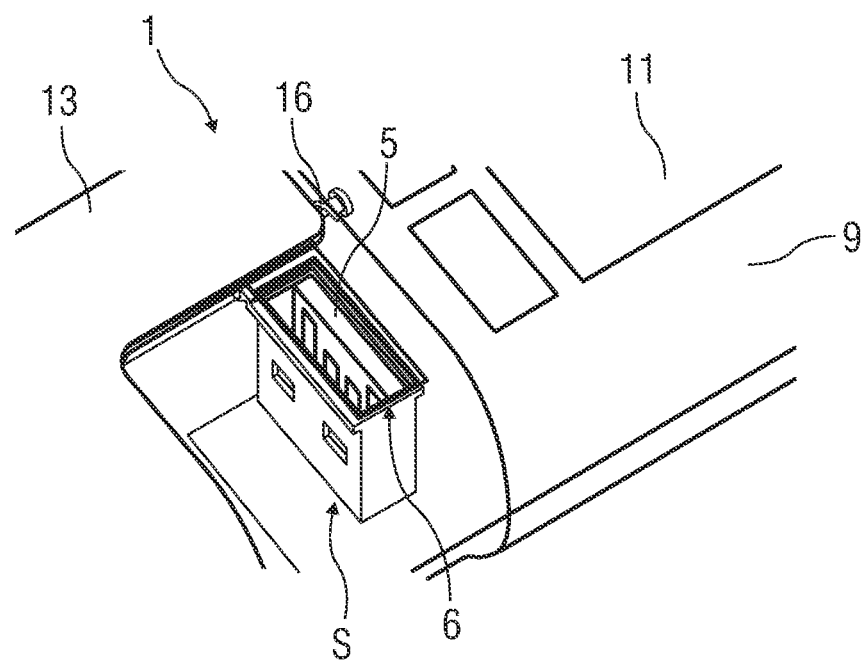
FIG. 17 is a schematic perspective view of the embodiment of FIG. 16 with the cap attached to the body and the port aligned with the recess.

When the cap 13 is fitted to the body 9, the cap 13 directly actuates the motion of the port 5, such that when the cap 13 is removed the port 5 is misaligned with the recess 6 and inaccessible (FIG. 16) and when the cap 13 is attached to the body 9 the port 5 is aligned with the recess 6 in the body 9 and thus accessible (FIG. 17). A first spring 16 is used to ensure a default state of the system with no cap 13 fitted is to move the port 5 such that it is misaligned with the recess 6. A sliding cover 12 may be additionally attached to the port 5 for covering the recess when the cap 13 is removed and the port 5 is misaligned with the recess 6.

Figure 18:
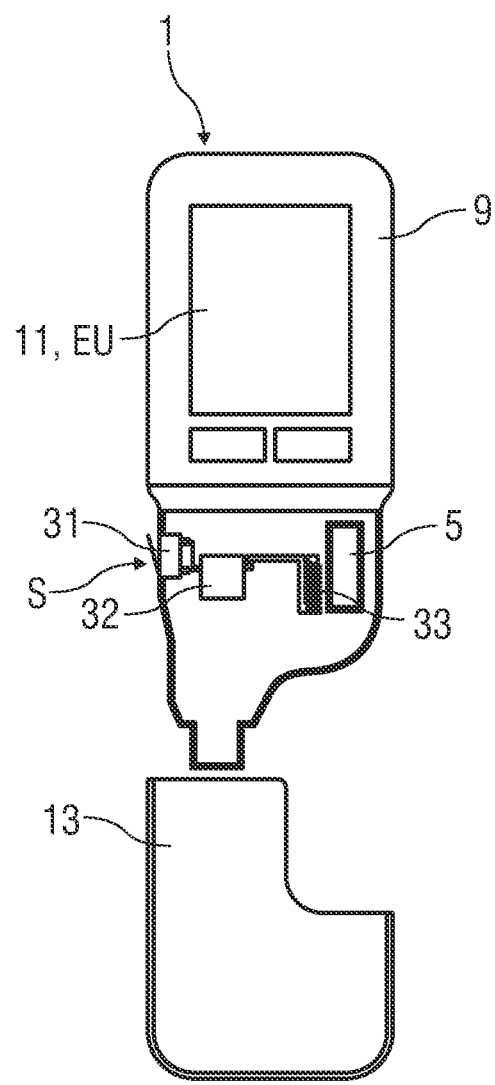
FIG. 18 is a schematic view of an exemplary embodiment of a drug delivery device with an electromechanical safety mechanism.

FIG. 18 is a schematic view of an exemplary embodiment of a drug delivery device 1 with an electromechanical safety mechanism.

The drug delivery device 1 comprises a body 9 adapted to receive a drug cartridge or syringe (not illustrated). A hypodermic needle (not illustrated) may be attached to the cartridge. The drug delivery device 1 may comprise a human-machine-interface 11 for communicating information to a user and for allowing the user to operate the drug delivery device 1. Furthermore, the drug delivery device 1 may comprise an electromechanical drive (not illustrated) for inserting the needle into an injection site, e.g. a patient's skin and/or dispensing drug from the cartridge through the needle and/or retracting the needle post-injection.

The drug delivery device 1 comprises a port 5 which may serve for wired communication with another device for data transfer or charging. The port 5 is arranged in the body 9 of the drug delivery device 1. A sliding cover (not illustrated) may be arranged to hide the port 5 when in a closed position or expose the port 5 when in an open position relative to the body 9. Likewise the port 5 may be moveably arranged within the body 9 such that it may be aligned or misaligned with a recess in the body 9 thus rendering the port 5 accessible or inaccessible.

A cap 13 is arranged to be assembled over the needle and over part of the body 9 such that the needle is inaccessible when the cap 13 is attached to the body 9.

A switch 31 is arranged in the body 9 for detecting whether the cap 13 is attached to the body 9 or not. Fitting the cap 13 to the body 9 triggers the switch 31 which, via a control circuit 32, releases a retaining mechanism 33 for moving the cover 12 and/or the port 5 for rendering the port 5 accessible. If the cap 13 is not attached the switch 31 triggers the retaining mechanism 33 via the control circuit 32 to restore the cover 12 and/or the port 5 to a position where the port 5 is inaccessible.

The retaining mechanism 33 may be arranged as a solenoid arranged for holding the cover 12 in the closed position CP when energized and to release the cover 12 to move into the open position OP when not energized.

Likewise the retaining mechanism 33 may be arranged as a motor or other linear actuator to directly drive the movement of the cover 12 to open and close the port 5.

Alternatively, the retaining mechanism 33 may drive the movement of the port 5.

The aforementioned embodiments may be modified to prevent removal of the cap 13 while a connector is connected to the port 5 thus encouraging the user to remove the connector before removing the cap 13. This prevents the user from exposing the needle while the port 5 is being accessed.

Figure 19:
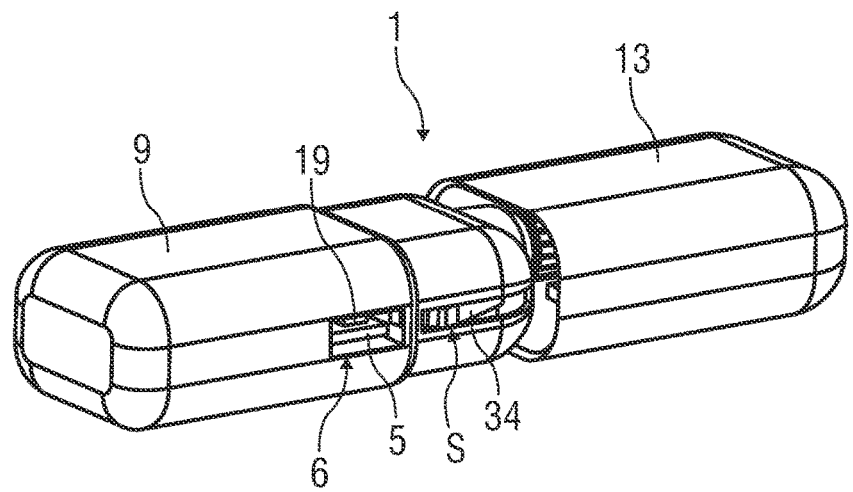
FIG. 19 is a schematic view of an exemplary embodiment of a drug delivery device with a cap removed from the body and a blocking component extending into a recess.

FIG. 19 is a schematic view of an exemplary embodiment of a drug delivery device 1 with a safety mechanism.

The drug delivery device 1 comprises a body 9 adapted to receive a drug cartridge or syringe (not illustrated). A hypodermic needle (not illustrated) may be attached to the cartridge. The drug delivery device 1 may comprise a human-machine-interface (not illustrated) for communicating information to a user and for allowing the user to operate the drug delivery device 1. Furthermore, the drug delivery device 1 may comprise an electromechanical drive (not illustrated) for inserting the needle into an injection site, e.g. a patient's skin and/or dispensing drug from the cartridge through the needle and/or retracting the needle post-injection.

The drug delivery device 1 comprises a port 5 which may serve for wired communication with another device for data transfer or charging. The port 5 is arranged within a recess 6 in the body 9 of the drug delivery device 1. A blocking component 19 biased by a first spring 16 is arranged to protrude into the recess 6 to prevent a connector from connecting to the port 5.

A cap 13 is arranged to be assembled over the needle and over part of the body 9 such that the needle is inaccessible when the cap 13 is attached to the body 9.

Figure 20:
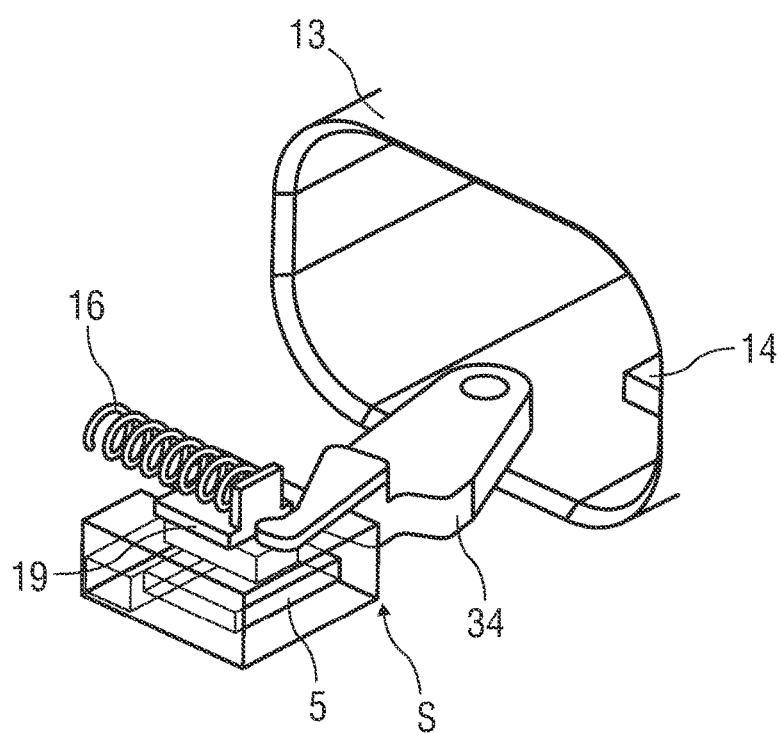
FIG. 20 is another schematic view of the embodiment of FIG. 19 with the cap removed from the body and the blocking component extending into the recess.

When the cap 13 is removed from the body 9, the first spring 16 moves the blocking component 19 such that it extends into the recess 6 and prevents a connector from being inserted into the port 5 as illustrated in FIGS. 19 and 20.

Figure 21:
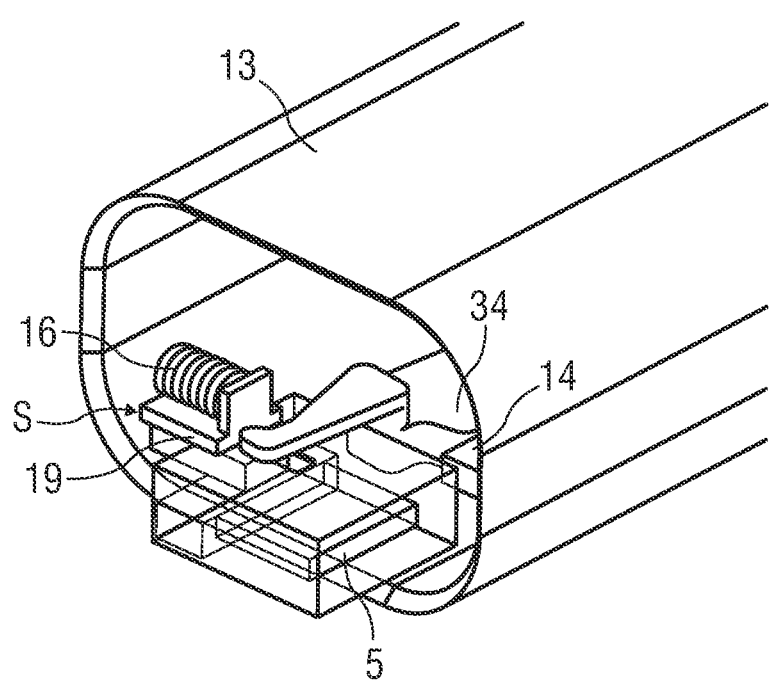
FIG. 21 is another schematic view of the embodiment of FIG. 19 with the cap attached and the blocking component moved inwards to clear the recess.

When the cap 13 is attached the tab 14 acts on a surface of a pivot arm 34 to force the blocking component 19 inwards to clear the recess 6, allowing a connector to be fitted to the port 5 (see FIG. 21).

Figure 22:
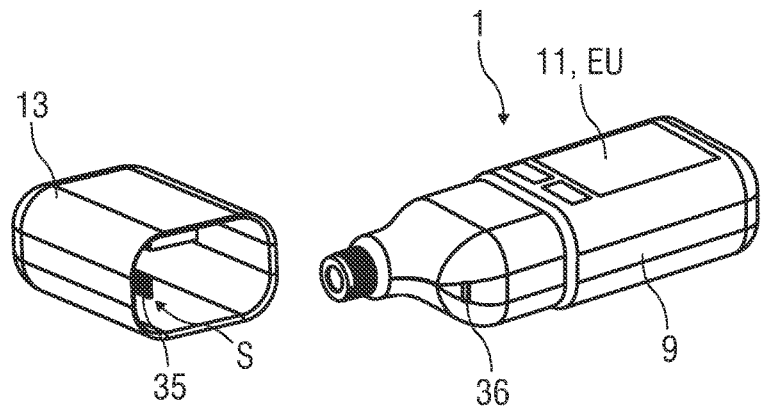
FIG. 22 is a schematic view of an exemplary embodiment of a drug delivery device with a safety mechanism and a cap.

FIG. 22 is a schematic view of an exemplary embodiment of a drug delivery device 1 with a safety mechanism.

The drug delivery device 1 comprises a body 9 adapted to receive a drug cartridge or syringe (not illustrated). A hypodermic needle (not illustrated) may be attached to the cartridge. The drug delivery device 1 may comprise a human-machine-interface 11 for communicating information to a user and for allowing the user to operate the drug delivery device 1. Furthermore, the drug delivery device 1 may comprise an electromechanical drive (not illustrated) for inserting the needle into an injection site, e.g. a patient's skin and/or dispensing drug from the cartridge through the needle and/or retracting the needle post-injection.

A cap 13 is arranged to be assembled over the needle and over part of the body 9 such that the needle is inaccessible when the cap 13 is attached to the body 9. The drug delivery device 1 comprises a port 5 which may serve for wired communication with another device for data transfer or charging. The port 5 is arranged within the cap 13. A customized interface between the body 9 and the cap 13 comprising a customized connector 35 and a customized second port 36 is arranged to connect the port 5 to the circuitry in the body 9 when the cap 13 is attached to the body 9.

The port 5 can therefore only be used when the cap 13 is fitted to the body 9. When the cap 13 is not fitted the port 5 remains accessible. However, the port 5 is not connected to any of the electronics on the drug delivery device 1, mitigating the risk.

Figure 23:
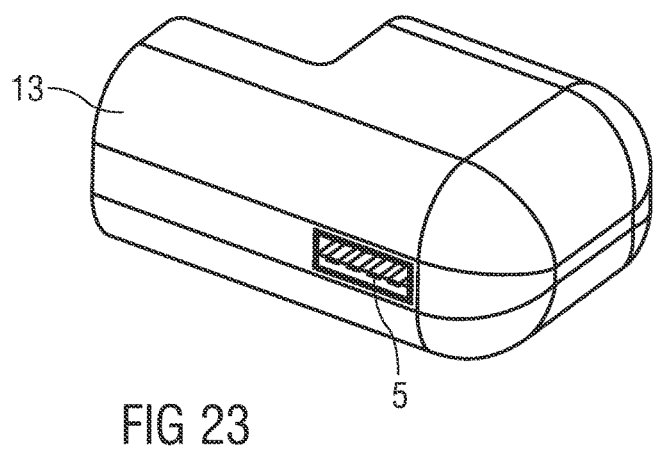
FIG. 23 is a perspective schematic view of the cap of the embodiment of FIG. 22.

FIG. 23 is a perspective schematic view of the cap 13 of this embodiment.

When the cap 13 is fitted to the body 9, the customized connector 35 is inserted in the customized second port 36 or connector slot, the aperture of which is small enough as to prevent it posing a risk to the user that they might accidentally come into contact with the customized second port 36.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39),

-continued des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);

or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, -continued H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:
1. Drug delivery device for administering a drug, comprising:
  a body,
  at least one electrical unit and a port for electrically contacting the at least one electrical unit,
  an adapter for attaching an injection needle to the drug delivery device,
  a safety mechanism comprising a cap arranged to be assembled over the injection needle and over part of the body such that the injection needle is inaccessible and the port is accessible when the cap is attached to the body, wherein the port is inaccessible when the cap is removed from the body,
  wherein the port is arranged within a recess in the body, wherein the safety mechanism comprises a cover arranged to hide the recess when in a closed position or expose the recess when in an open position relative to the body, wherein a cap is arranged to be assembled over the injection needle and over part of the body such that the injection needle is inaccessible when the cap is attached to the body, whereas the recess with the port remains uncovered, wherein the cap, when mounted to the body, is arranged to cause movement of the cover into the open position and/or unlock the cover for allowing its movement into the open position,
  wherein a blocking component is slidably arranged in the body and biased towards a blocking position for preventing the cover to be moved out of the closed position, wherein the cap, when attached to the body, is arranged to move the blocking component out of the blocking position thus allowing movement of the cover towards the open position,
  wherein the blocking component is shaped as a spring, wherein the cover is shaped substantially cylindrical, rotatably fitted to the body and comprises an opening for accessing the port, wherein when the cap is not fitted to the body, a retaining tongue on the spring engages with a retaining feature on the cover to prevent it from rotating out of the closed position, wherein a beam on the cap is arranged to push the spring out of engagement with the retaining feature when the cap is mounted to the body.

2. Drug delivery device according to claim 1, wherein a second spring is arranged to bias the cover towards the closed position.

3. Drug delivery device according to claim 1, wherein the cover is arranged to pivot or slide between the closed position and the open position.

4. Drug delivery device according to claim 1, wherein the cover is arranged to be locked in the closed position.

5. Drug delivery device according to claim 1, wherein a handle on the cover is arranged to interact with an opening in the cap such that the cap prevents rotation of the cover unless it is fully assembled to the body.

6. Drug delivery device according to claim 1, wherein the cap is arranged to be mounted to the body by an axial translation and/or a rotation.

7. Drug delivery device according to claim 1, wherein a switch is arranged in the body for detecting the cap such that assembling the cap to the body triggers the switch which causes release of a retaining mechanism for moving or allowing movement of the cover and/or the port into the open position for rendering the port accessible and that removal of the cap triggers the switch which causes the retaining mechanism to move the cover and/or the port into the closed position.

8. Drug delivery device according to claim 1, wherein the device is configured such that removal of the cap is prevented while a connector is connected to the port.

9. Drug delivery device for administering a drug, comprising:
a body,
at least one electrical unit and a port for electrically contacting the at least one electrical unit,
an adapter for attaching an injection needle to the drug delivery device,
a safety mechanism comprising a cap arranged to be assembled over the injection needle and over part of the body such that the injection needle is inaccessible and the port is accessible when the cap is attached to the body, wherein the port is inaccessible when the cap is removed from the body wherein the port is arranged within a recess in the body, wherein the safety mechanism comprises the port being movable relative to the body, wherein a cap is arranged to be assembled over the injection needle and over part of the body such that the injection needle is inaccessible when the cap is attached to the body, whereas the recess with the port remains uncovered, wherein the cap, when mounted to the body, is arranged to cause movement of the port into alignment with the recess in an open position and wherein the port moves into misalignment with the recess when the cap is removed from the body.

* * * * *

UNITED STATES PATENT AND TRADEMARK OFFICE
CERTIFICATE OF CORRECTION

PATENT NO. : 10,064,996 B2
APPLICATION NO. : 14/763863
DATED : September 4, 2018
INVENTOR(S) : Draper et al.

Page 1 of 1

It is certified that error appears in the above-identified patent and that said Letters Patent is hereby corrected as shown below:

On the Title Page

Item (72), delete "Simon Bilton Lewis" and insert -- Simon Lewis Bilton --

Signed and Sealed this
Twenty-seventh Day of November, 2018

Andrei Iancu
*Director of the United States Patent and Trademark Office*